US011058596B2

(12) United States Patent
Kumar et al.

(10) Patent No.: US 11,058,596 B2
(45) Date of Patent: Jul. 13, 2021

(54) AUTOREGULATION OF IRRADIANCE IN PHOTOTHERAPY SYSTEMS

(71) Applicant: GENERAL ELECTRIC COMPANY, Schenectady, NY (US)

(72) Inventors: Anand Kumar, Dubai (AE); Jikku Philip, Bangalore (IN); Sirosh Sivasankaran, Bangalore (IN)

(73) Assignee: General Electric Company, Schenectady, NY (US)

( * ) Notice: Subject to any disclaimer, the term of this patent is extended or adjusted under 35 U.S.C. 154(b) by 403 days.

(21) Appl. No.: 16/020,660

(22) Filed: Jun. 27, 2018

(65) Prior Publication Data
US 2019/0000704 A1 Jan. 3, 2019

(30) Foreign Application Priority Data

Jun. 28, 2017 (IN) .............................. 201741022697

(51) Int. Cl.
*A61G 11/00* (2006.01)
*A61N 5/06* (2006.01)

(52) U.S. Cl.
CPC ............ *A61G 11/00* (2013.01); *A61G 11/005* (2013.01); *A61N 5/0621* (2013.01); *A61G 2203/46* (2013.01); *A61G 2210/90* (2013.01); *A61N 2005/0626* (2013.01); *A61N 2005/0628* (2013.01); *A61N 2005/0637* (2013.01); *A61N 2005/0652* (2013.01)

(58) Field of Classification Search
CPC .. A61G 11/00; A61G 11/005; A61G 2203/46; A61G 2210/90; A61N 5/0621; A61N 2005/0626; A61N 2005/0628; A61N 2005/0637; A61N 2005/0652
USPC ........................................................ 607/90
See application file for complete search history.

(56) References Cited

U.S. PATENT DOCUMENTS

| | | | |
|---|---|---|---|
| 7,357,811 B2 | 4/2008 | Dykes et al. | |
| 8,267,922 B2 | 9/2012 | Hodge et al. | |
| 9,205,278 B2 | 12/2015 | Gophlakrishnan et al. | |
| 2007/0162091 A1 | 7/2007 | Hodge | |
| 2010/0179469 A1* | 7/2010 | Hammond | A61N 5/0624 604/20 |
| 2012/0296260 A1* | 11/2012 | Vizethum | A61N 5/062 604/20 |
| 2016/0016001 A1* | 1/2016 | Loupis | A61N 5/0616 604/20 |

* cited by examiner

*Primary Examiner* — Aaron F Roane

(57) ABSTRACT

A device for providing phototherapy. The device has lights that emit irradiance to provide phototherapy. The lights are positionable to emit the irradiance towards a patient. An enclosure is connected to a base and supports the lights. A control module is operatively connected to the lights and controls the irradiance emitted from the lights. A non-transitory memory module is operatively connected to the control module and stores a control program. A plurality of sensors is operatively connected to the control module and are configured to sense a current position of the lights. The control program is configured to receive inputs that include at least the current position of the lights and to provide outputs to the control module based at least in part on the inputs. The control module controls the irradiance emitted from the plurality of lights based at least in part on the outputs.

19 Claims, 7 Drawing Sheets

AUTOREGULATION OF IRRADIANCE IN PHOTOTHERAPY SYSTEMS

FIELD the present disclosure generally relates to phototherapy systems, and more particularly to autoregulation of irradiance in phototherapy systems for medical treatment.

BACKGROUND

The background and summary are provided to introduce a foundation and selection of concepts that are further described below in the detailed description. The background and summary are not intended to identify key or essential features of the claimed subject matter, nor are they intended to be used as an aid in limiting the scope of the claimed subject matter.

The following U.S. Patents and patent applications are incorporated herein by reference:

U.S. Pat. No. 7,357,811 discloses an infant warming apparatus for supporting an infant upon an infant platform. The apparatus has a procedure light that is recessed into the normal horizontal overhead housing of the apparatus and thus integrated into the infant apparatus. The procedure light is conveniently located above and centrally positioned with respect to the infant so as to direct the light toward the infant. The mounting provides omnidirectional movement of the procedure light and the movement can be easily controlled by means of a control handle that extends downwardly with a distal end readily accessible to the caregiver. At or proximate to the distal end there is an electrical controller to enable the caregiver to change the intensity of the light beam. The light beam can also be easily focused so as to allow the caregiver to direct the desired beam of light onto the area of interest of the infant.

U.S. Pat. No. 8,267,922 a phototherapy light device for directing light onto an infant. The phototherapy light device has a base containing an illumination source and a gooseneck type of elongated neck that extends outwardly from the base and has a distal end adapted to be positioned to direct the light onto the infant. An optical fiber transmits the light from the illumination source to the distal end through the optical fiber where the light is passed through a light emanating device located at the distal end of the elongated neck. The elongated neck has two flexible sections, one of which has two coaxial springs to provide flexibility in positioning as well as to impart sufficient strength and rigidity to the elongated neck. The dual spring concept provides a system having reduced stresses while creating a double fault structural system without compromising the flexibility of the elongated neck.

U.S. Pat. No. 9,205,278 discloses a method of computing peak spectral irradiance, the method comprising characterizing at least one light source to determine an irradiance distribution pattern, generating multiple density cones in a three dimensional model based on the irradiance distribution pattern, positioning the multiple density cones in a desired layout, measuring density of irradiance at one or more locations, and optimizing the positioning of the at least one light source to obtain a desired irradiance distribution.

U.S. Patent application publication no. 2007/0162091 discloses a phototherapy light device for directing light onto an infant. The phototherapy light device has a base containing an illumination source and a gooseneck type of elongated member that extends outwardly from the base and has a conical shaped shade at its distal end. An optical fiber transmits the light from the illumination source to the shade through the optical fiber where the light is passed through a plastic fresnel lens at the distal end of the shade. By the use of the fresnel lens and the means of affixing the shade onto the elongated member, the distal end of the phototherapy light device is relatively light and which alleviates the problem of that distal end sagging downwardly to contact the infant undergoing treatment.

SUMMARY

One embodiment of the present disclosure generally relates to a device configured to provide phototherapy to a patient. The device is configured to be supported by a base on the ground and has a plurality of lights configured to emit irradiance to provide phototherapy. The plurality of lights are positionable to emit the irradiance towards the patient. An enclosure is connected to the base and supports the plurality of lights. A control module is operatively connected to the plurality of lights and controls the irradiance emitted from the plurality of lights. A non-transitory memory module is operatively connected to the control module. A plurality of sensors are operatively connected to the control module and are configured to sense a current position of the plurality of lights. A control program is configured to receive inputs and to provide outputs. The non-transitory memory module stores the control program. The inputs include at least the current position of the plurality of lights and the control program determines the outputs based at least in part on the inputs. The outputs are provided by the control program to the control module and the control module controls the irradiance emitted from the plurality of lights based at least in part on the outputs provided by the control program.

Another embodiment generally relates to a method for providing phototherapy to a patient. The method includes positioning a plurality of lights to emit irradiance towards the patient and operatively connecting a control module to the plurality of lights, where the control module controls the irradiance emitted from the plurality of lights. The method further includes operatively connecting a non-transitory memory module to the control module and operatively connecting a plurality of sensors to the control module. The method further includes sensing with the plurality of sensors a current position of the plurality of lights, storing a control program within the non-transitory memory, and configuring the control program to receive inputs and to provide outputs. The inputs include at least the current position of the plurality of lights. The method further includes determining with the control program the outputs based at least in part on the inputs received by the control program and providing the outputs to the control module, and controlling with the control module the irradiance emitted from the plurality of lights based at least in part on the outputs provided by the control program.

Another embodiment generally relates to a device configured to provide phototherapy to a patient. The device is configured to be supported by a base on the ground and includes an array of light emitting diodes (LEDs) configured to emit irradiance to provide phototherapy. The array of LEDs are positionable to emit the irradiance towards the patient. An enclosure is connected to the base and supports the array of LEDs and a control module is operatively connected to the array of LEDs. The control module controls the irradiance emitted from the array of LEDs. A non-transitory memory module is operatively connected to the control module and stores a control program. The control program is configured to receive inputs and to provide outputs. A plurality of sensors is operatively connected to the control module and configured to sense a current position of the array of LEDs. The current position includes an angle between the array of LEDs and the base and a height between the array of LEDs and the ground and a distance between the array of LEDs and the patient. The current position of the array of LEDs is one input of the inputs received by the control program. The control program determines the outputs based at least in part on the inputs received by the control program and the outputs are provided by the control program to the control module. The control module controls the irradiance emitted from the plurality of lights based at least in part on the outputs provided by the control program.

Various other features, objects and advantages of the disclosure will be made apparent from the following description taken together with the drawings.

BRIEF DESCRIPTION OF THE DRAWINGS

The drawings illustrate the best mode presently contemplated of carrying out them disclosure. The same numbers are used throughout the drawings to reference like features and like components. In the drawings.

DETAILED DISCLOSURE

Figure 1:
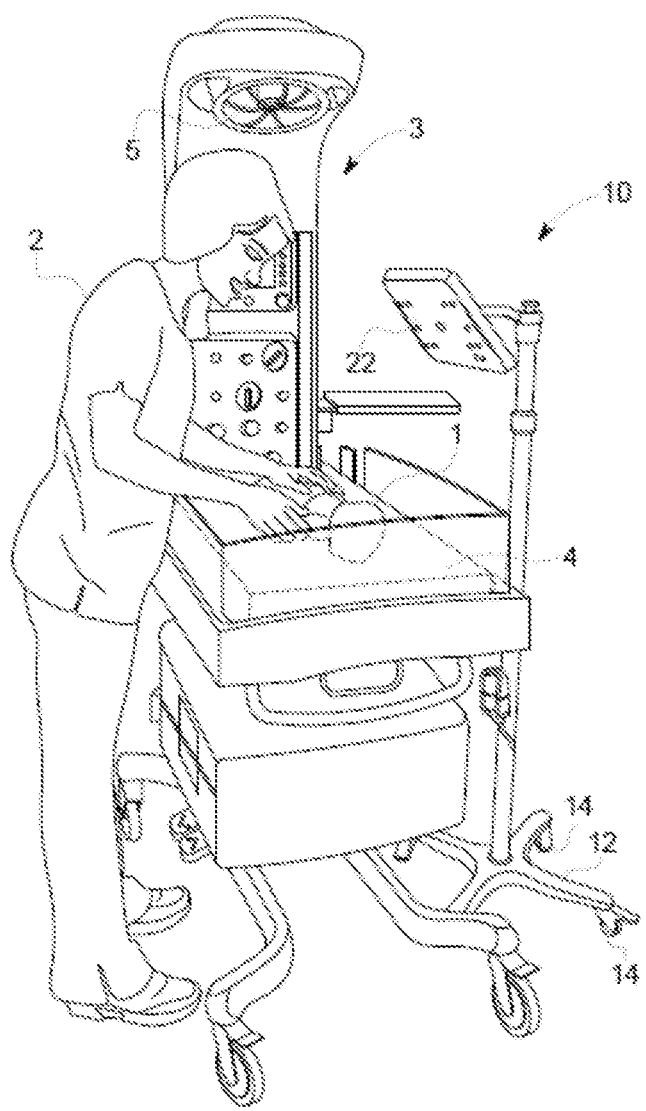
FIG. 1 depicts the presently disclosed device in use alongside an external care device known in the art.

This written description uses examples to disclose embodiments of the present application, including the best mode, and also to enable any person skilled in the art to practice or make and use the same. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Phototherapy is a common medical intervention for treating patients, which is often used for the treatment of jaundice in newborn patients. Neonatal jaundice, or neonatal hyperbilirubinemia, presents as a yellowing of the skin and other tissues caused by elevated levels of bilirubin in the body. Controlled exposure to light, the intent of phototherapy, assists in breaking down this excess of bilirubin while the patient continues to develop. Once fully developed, the patient is typically able to maintain healthy bilirubin levels without intervention.

The present inventors have recognized that current phototherapy devices known in the medical industry provide static irradiance levels, meaning that the phototherapy device emits or outputs a static level of irradiance. These devices known in the art have specified distances to be placed from the patient and are to be positioned at a right angle to, or to direct the irradiance directly towards, the patient. Some devices allow the level of irradiance emitted to be manually adjustable, which effectively incorporate manual dimmer switches. However, when phototherapy devices are used in actual clinical settings, the devices are often placed at oblique angles to the patient and varying height levels as compared to the manufacturer's specification. This obliquity and incorrect height placement is caused by the fact that phototherapy devices are often used in conjunction with other treatments being provided to the newborn, such as the newborn being placed within a radiant warmer or in an infant incubator. Using these phototherapy devices in conjunction with other external care devices such as these leads to uneven and non-uniform irradiance, which often results in lower levels of irradiance being received by the newborn resting on the bed. This lower level of irradiance in turn delays the bilirubin break down, causing an increased length of stay or additional intervention, such as exchange transfusion.

It should be recognized that the device 10 may also incorporate controls to manually adjust irradiance; however, the irradiance emitted would nonetheless be controlled by the control module 30 to compensate for changes in position, angle, and other factors discussed herein.

In addition, the development of led technology and its integration into phototherapy devices has presented new challenges with providing uniform, consistent, and accurate irradiance. Specifically, the flux range, or light intensity, of LEDs slowly degrades over the life of use. In other words, presently known devices do not provide consistent irradiance over the lifetime of the device.

The present disclosure relates to devices and methods for autoregulation of irradiance in phototherapy systems using smart sensing and algorithm-based controls for compensating or adjusting irradiance based on angular obliqueness in the placement of the phototherapy system in reference to the patient or patient bed. Furthermore, the presently disclosed devices and systems compensate for any variations arising from changes in the distance or angle from the light source to the patient or patient bed in clinical use settings, including horizontal placement and/or the vertical height from the ground. The system provides this sensing and compensation through multiple sensor inputs to auto-regulate the device through a closed-loop control system, providing real-time irradiance output of the plurality of lights in delivering the phototherapy. As a result, the present disclosure emits irradiance towards the newborn alongside other therapeutic interventions in a known and consistent manner, thereby reducing the effective stay for phototherapy treatments.

FIG. 1 depicts the presently disclosed device 10 being used to treat a patient 1 that is concurrently receiving treatment from an external care device 3. As shown, the patient 1 rests on a bed 4 within the external care device 3, which provides further treatment as a radiant warmer through the heating unit 5 overhead. Both the device 10 and the external care device 3 provide treatment to the patient 1 while not impeding the ability of further monitoring and treatment of the patient 1 by the caregiver 2.

In the embodiment shown, the device 10 includes a plurality of lights 22 configured to emit irradiance to provide phototherapy to the patient 1. In this embodiment, the device 10 is supported on the ground by a base 12 and is movable on the ground by a plurality of castors 14 for positioning and storage.

Figure 2:
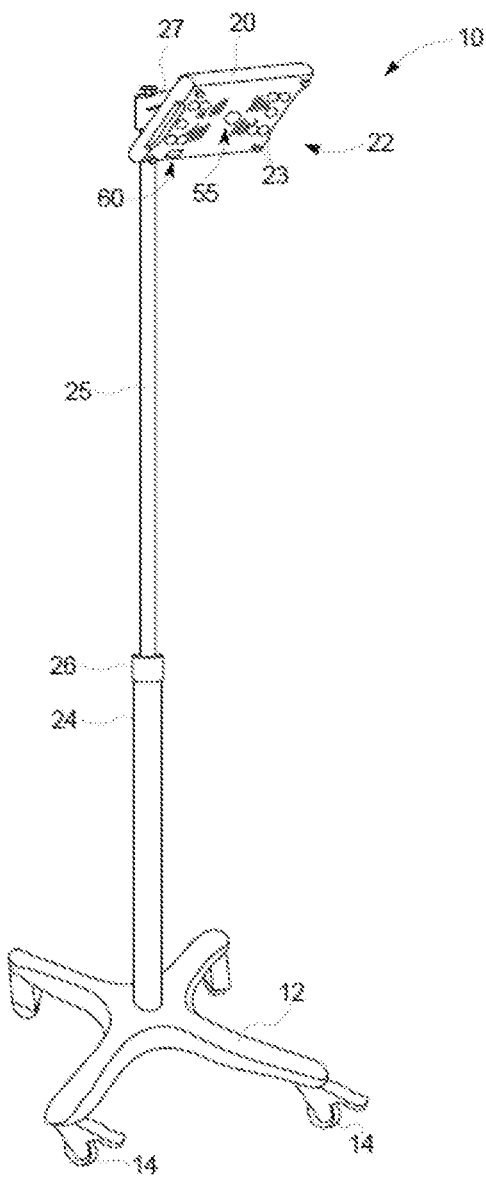
FIG. 2 is a perspective view of the device similar to that shown in FIG. 1.

In the embodiment of FIG. 2, the plurality of lights 22 is an array of LEDs comprised of individual light emitters 23. The plurality of lights 22 is supported by an enclosure 20 that is connected to a base 12 via an arm 27 and an outside support 24 and inside support 25 coupled with a lock 26 therebetween. FIG. 2 further shows a distance sensor 55, shown here as an optical sensor, configured to sense a distance between the plurality of lights 22 and the patient 1, which is discussed further below. The embodiment shown further depicts an indicator 60 configured to provide an indication to the caregiver 2 when at least one of the individual light emitters 23 is not performing within an allowable performance threshold, which is also discussion further below.

Figure 3:
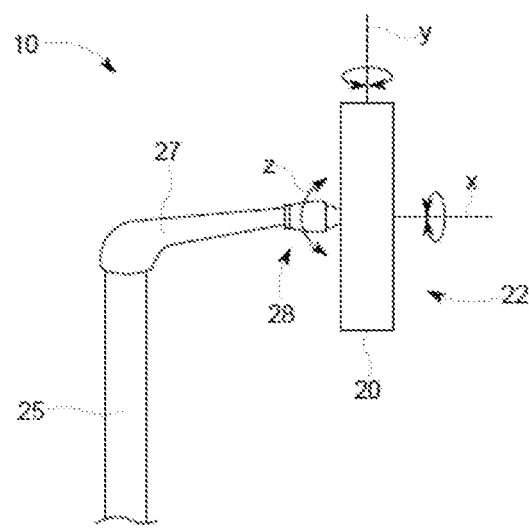
FIG. 3 is a close up, side view of another embodiment of the presently disclosed device from FIG. 1.

FIG. 3 shows a side view of a device similar to that shown in FIG. 2, particularly demonstrating the adjustable positioning of the enclosure 20 relative to the arm 27. Specifically, a pivot joint 28 connected between the arm 27 and the enclosure 20 allows the enclosure 20 to rotate about the x axis, turn about the y axis, or tilt as indicated by the z arrow. It should be recognized that other structures for positioning the enclosure 20 would be known to one of ordinary skill in the art.

Figure 4:
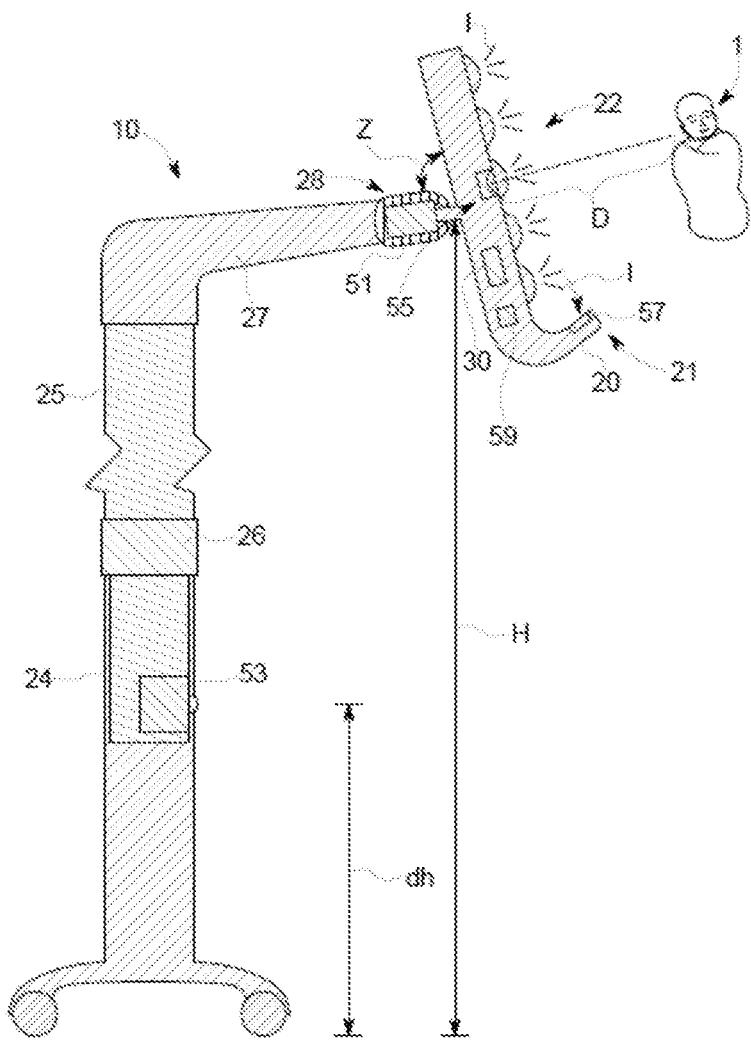
FIG. 4 is a sectional view of another embodiment of a device similar to the device shown in FIG. 3.

FIG. 4 depicts a cut-away sectional view of an embodiment similar to that shown in FIG. 3. The embodiment of FIG. 4 includes a lower edge 21 of the enclosure 20 that extends outwardly and upwardly such that an irradiance sensor 57 can be positioned in the lower edge 21 to detect the irradiance i of light being emitted by the plurality of lights 22. FIG. 4 further shows the distance sensor 55 shown in FIG. 2, whereby the distance sensor 55 senses the distance x between the plurality of lights 22 and a target, in this case, the patient 1. It should be recognized that other targets may be included in addition to, or instead of the patient, such as features on a bed 4 or a specialized pattern on a sticker.

A height sensor 53 is also shown, which in this embodiment is an encoder with a rolling wheel, which determines the displacement height dh between the height sensor 53 and the ground. This displacement height dh can be used to infer the height H of the plurality of lights 22 above the ground by knowing the structures of the outside support 24, the inside support 25, the arm 27, the enclosure 20, and the placement of the plurality of lights 22 therein. Coupled with a known or average bed height, the height h can then determine the vertical distance from the plurality of lights 22 to the patient 1.

In other embodiments, the height sensor 53 may be a piezo-electric sensor, a slide-based sensor, or other sensors known in the art. Similarly, while the present embodiment shows an optical sensor as the distance sensor 55, one of ordinary skill in the art would recognize that other technologies, such as infrared sensors or photo sensors, could also be used to determine the distance d between the plurality of lights 22 and the patient 1.

FIG. 4 further depicts an angle sensor 51 positioned within the pivot joint 28 connecting the enclosure 20 to the arm 27. The angle sensor 51, which is shown here as an inclinometer, detects the position of the enclosure 20, and thus the plurality of lights 22 relative to the arm 27, in the x, y, and z directions shown in FIG. 3. In the present context of the device 10 competing for space with the external care device 3, the angle of greatest interest is often the tilt of the enclosure 20 as shown by the z arrow.

It should be recognized that information from a portion of the plurality of sensors 50 can be used to infer information that could be sensed with others. For example, determining the angle z between the plurality of lights 22 and the base 12 and the distance from the plurality of lights 22 to the patient 1, the horizontal and vertical position of the plurality of lights 22 can be determined. In this manner, the device 10 need not have all types of the sensors disclosed herein. Alternatively, information from sensors may be combined and compared with redundant information sources to confirm functionality and performance of the various sensors.

As previously stated, the irradiance emitted by the plurality of lights 22 is not static over time, but typically degrades over the life of the device 10 and, specifically, the life of the individual light emitters 23 within the plurality of lights 22. The present inventors have identified that medical practitioners using phototherapy systems presently known in the art often attempt to compensate for degradation of irradiance over time, as well as for obliqueness and distance to the patient 1, by simply setting the device to emit the maximum irradiance. Essentially, this is an effort to avoid under-exposure for treating the patient. However, as would be recognized by one of ordinary skill in the art, this practice often leads to over-irradiation of the patient 1, uneven irradiation of the patient due to obliqueness, and a reduced lifespan for the plurality of lights 22 from over powering.

Certain embodiments further incorporate an irradiance sensor 57, which may be a photo sensor known in the art, to sense the irradiance actually being emitted by the plurality of lights 22. Specifically, the device 10 compensates for variations between the actual irradiance emitted by the individual light emitters 23 relative to the desired or intended irradiance, as well as for the position of the device 10 relative to the patient 1, by regulating control of the plurality of lights 22. In certain embodiments, the device 10 controls of each individual light emitter 23 independently to optimize and compensate for the individual emission corresponding to each individual light emitter 23 and its position.

Figure 5:
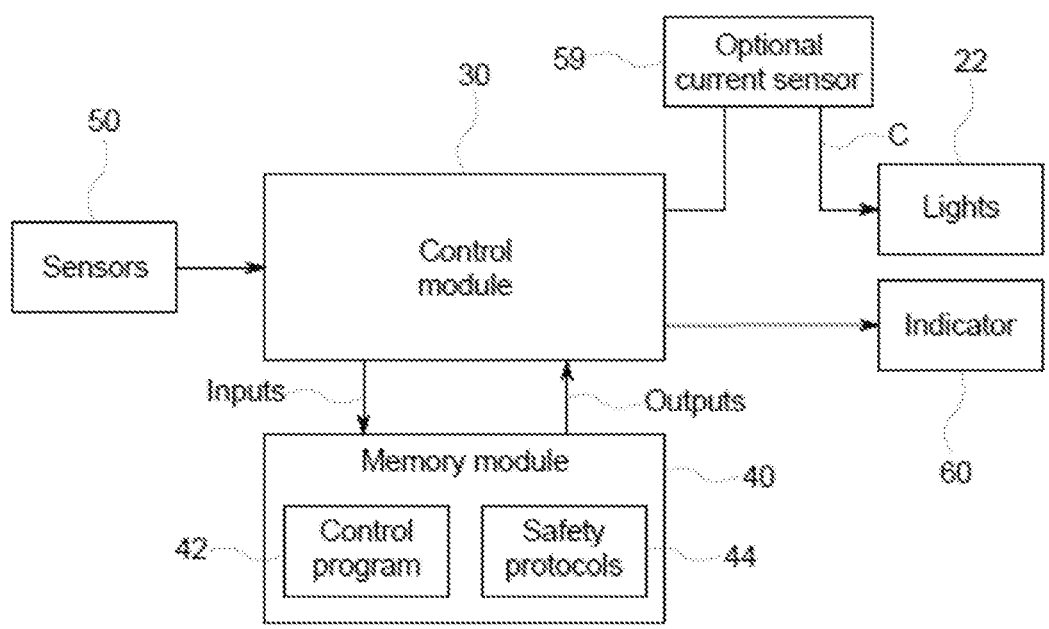
FIG. 5 is a schematic depiction of one embodiment of a system for regulating irradiance in accordance with the present disclosure.

FIG. 5 shows a schematic view of one embodiment of the present device 10 using inputs from the plurality of sensors 50. In the schematic, the lines depict one possible configuration of connections and are not limiting on the device or method. Other configurations, as well as divisions or combinations of functions in the structures shown, are anticipated by the present disclosure.

In the embodiment shown, a control module 30 is operatively connected to the plurality of lights 22 such that the control module 30 controls the irradiance emitted from the plurality of lights 22 by controlling the current delivered thereto. As previously stated, the control module 30 may control each of the individual light emitters 23 independently, in subsets, or all together. A non-transitory memory module 40 is operatively connected to the control module 30 and also to the plurality of sensors 50 configured to sense the current position of the plurality of lights 22. A control program 42 that is configured to receive inputs and to provide outputs is stored within the memory module 40. The control program 42 determines the outputs to provide to the control module 30 based at least in part on these inputs. The inputs at least include information from the plurality of sensors 50 received by the control module 30. The control program 42 also contains models based on empirical test results and known theoretical relationships relating to the obliquities and distances from the plurality of lights to the patient 1. Additional models within the control program 42 provide empirical and/or projected performance of various types of individual light emitters 23, such as fluorescent lights or LEDs, versus active hours of operation. The control program 42 applies the inputs from the plurality of sensors 50 to these models to provide the output to the control module 30. In turn, the control module 30 controls the irradiance I emitted from the plurality of lights 22 based at least in part on the outputs provided by the control program 42.

In some embodiments, the memory module 40 further stores safety protocols 44 configured to ensure that the device 10 does not cause irradiation beyond a safe limit for the patient 1 receiving phototherapy. The safety protocols 44 may include thresholds relating to the intensity of light, the duration of exposure, or various combinations and profiles thereof. Violation of these safety protocols 44 may automatically cause adjustments to autoregulate irradiance of the device 10, may generate an indication on the indicator 60, or both.

The embodiment of FIG. 5 includes a current sensor 59 that is operatively connected between the control module 30 and the plurality of lights 22. The current sensor 59 is configured to sense the current C flowing to the plurality of lights 22, which is monitored by the control module 30 at an instant and also over time. This monitoring information is compared against a replacement threshold stored within the memory module 40 such that the device 10 can determine the performance of each of the individual light emitters 23 over time. When the current C flowing to an individual light emitter 23 exceeds the replacement threshold, the indicator 60, which may be a led display visible from the enclosure 20, provides an indication that at least one of the plurality of lights 22 violates the replacement threshold and should be replaced. In other embodiments, each individual light emitter 23 may have its own indicator 60, such as a single led, to simplify the process of identifying which individual light emitter 23 is in violation of the replacement threshold, without requiring an LED display.

As previously stated, the plurality of sensors 50 may encompass a variety of sensors to determine the current position of the plurality of lights 22. In certain embodiments, the plurality of sensors 50 includes an angle sensor 51 to determine the angle between the plurality of lights 22 and the base 12, as previously discussed. In some embodiments, this angle sensor is an inclinometer. Alternatively or in addition, the plurality of sensors 50 may include a height sensor 53 to determine a height h between the plurality of lights 22 and the ground. As previously discussed, the displacement height dh may be sensed by a piezo-electric sensor, a rolling wheel encoder, or other sensors known in the art. Additionally or alternatively, the plurality of sensors 50 may include a distance sensor 55 configured to determine the distance D between the plurality of lights 22 and a target, such as the patient 1. In the embodiment shown, the distance sensor 55 is positioned centrally on the face of the enclosure 20 having the plurality of lights 22. However, other positions for placing the distance sensor 55 would be recognized by one of ordinary skill in the art.

As previously described, the plurality of sensors 50 may also include an irradiance sensor 57 to sense the actual irradiance being emitted by the plurality of lights 22. In the embodiment shown in FIG. 4, this encompasses a single irradiance sensor 57. However, a plurality of irradiance sensors 57 may be incorporated, including incorporating one for each of the individual light emitters 23 such that an actual irradiance can be determined individually.

Using the inputs from the plurality of sensors 50, the control program 42 provides outputs to the control module 30, which controls the irradiance emitted from the plurality of lights 22 based at least in part on these outputs. The plurality of lights 22 may be controlled individually or in groups as previously described.

Figure 6:
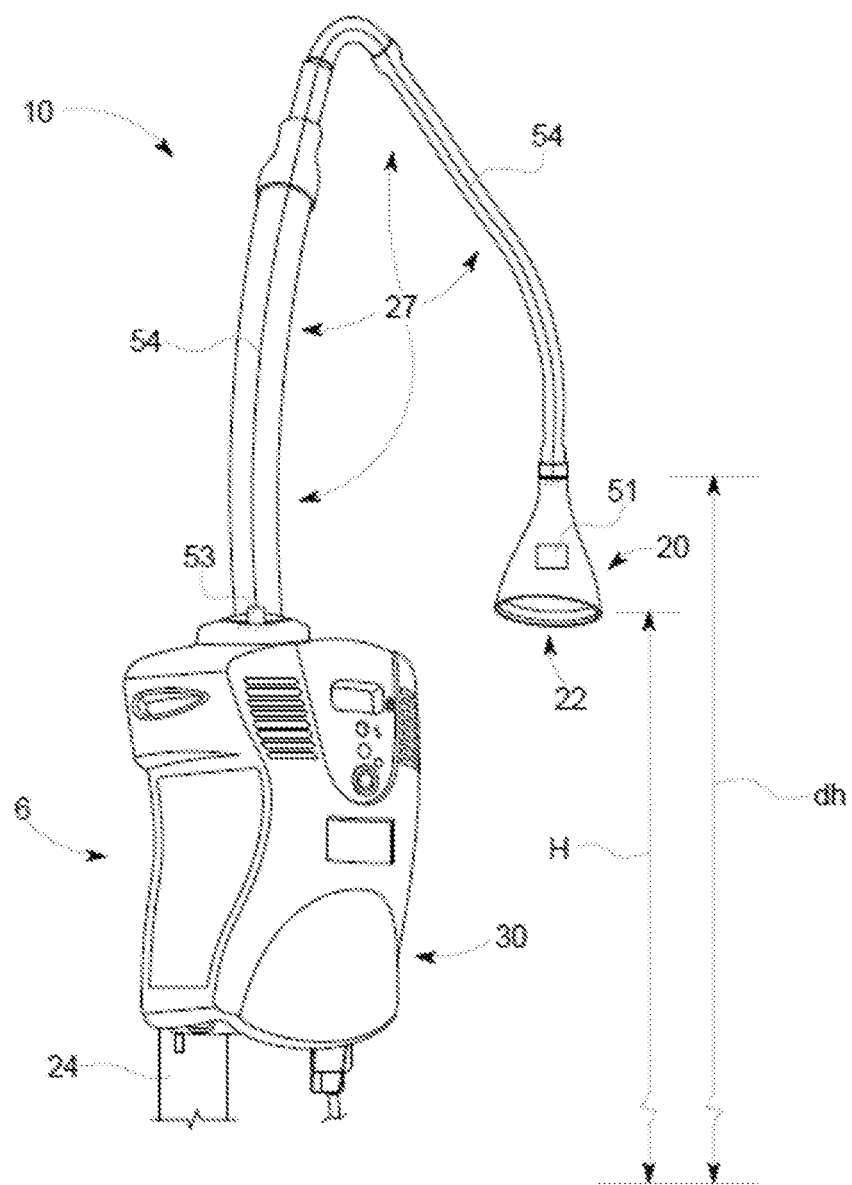
FIG. 6 is a perspective view of another embodiment in accordance with the present disclosure.
Figure 7:
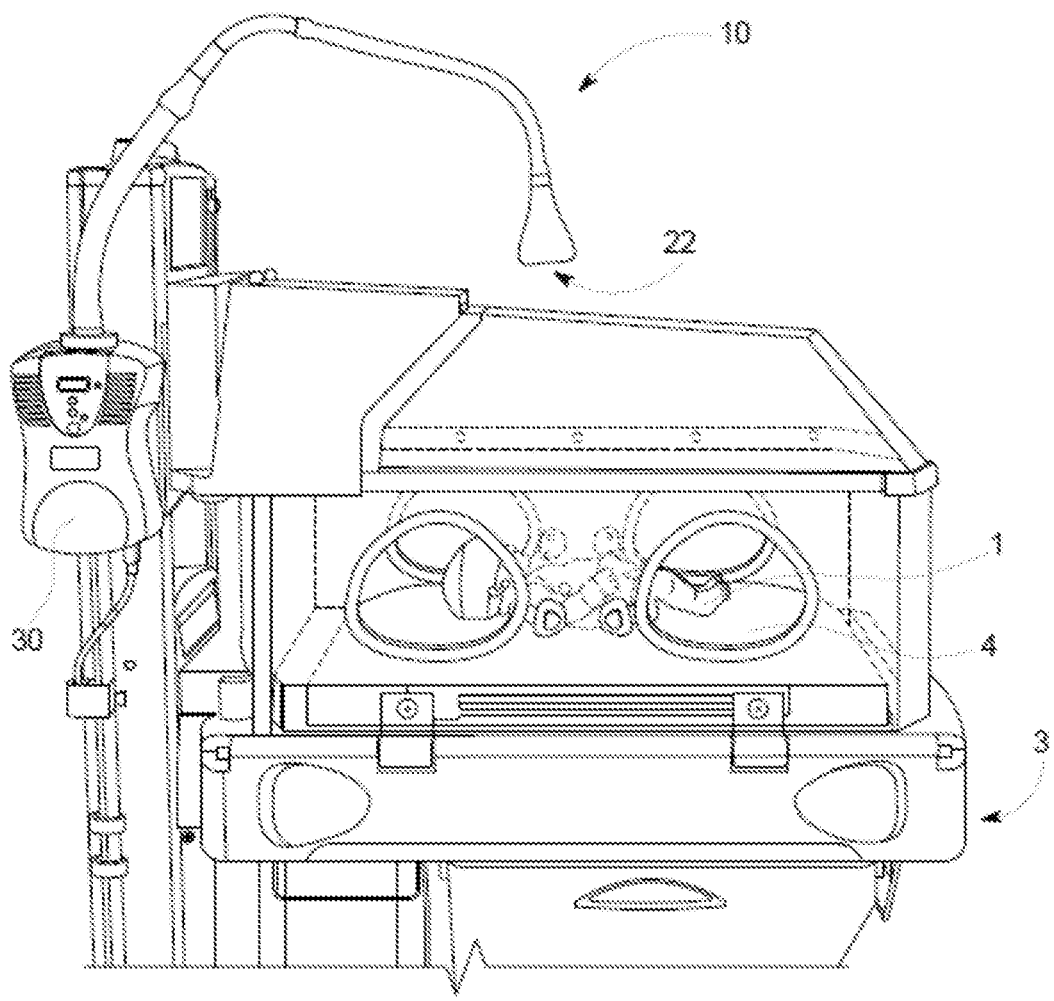
FIG. 7 depicts the device of FIG. 6 in use alongside an external care device known in the art.

FIGS. 6 and 7 depict an alternative embodiment of the device 10 providing autoregulation of irradiance during phototherapy. In this embodiment, the arm 27 is a flexible gooseneck for positioning the plurality of lights 22 to provide phototherapy to the patient 1. The enclosure 20 includes an angle sensor 51 to sense the orientation of the plurality of lights 22 in the x, y, and z directions. The angle sensor 51 may be a 3d position sensor as known in the art. Likewise, the present embodiment shows a height sensor 53, which here is coupled to a cable 54 running substantially from the height sensor 53 anchored to a main body 6 of the device 10 to the enclosure 20 within the arm 27. In this embodiment, the height sensor 53 determines the displacement height dh by sensing the tension on the cable 54 between the enclosure 20 and the height sensor 53. This displacement height dh can be used to infer the height h between the plurality of lights 22 and the ground.

Through experimentation and development, the present inventors have identified that the disclosed device provides optimal utilization and effectivity of irradiance emitted for bilirubin breakdown. This helps expedite the treatment of jaundice and reduces the length of stay for phototherapy. Furthermore, the presently disclosed device prevents user errors related to positioning, specifically by autoregulating the device to perform when the device is not positioned at an optimal distance between the plurality of lights 22 and the patient 1, including the angle therebetween.

In addition, the present inventors have identified that the presently disclosed device results in a lower total cost of ownership for the phototherapy device. This is provided by improving patient throughput by providing known effectiveness, thus avoiding the tendency for excessive, non-beneficial therapy time. The present disclosure further results in lowering power consumption and having a higher effective usage of led life by not over-powering the plurality of lights 22. As previously stated, many practitioners presently output the maximum irradiance to compensate for unknown output performance and to attempt to compensate for obliquity between the plurality of lights 22 and the patient 1.

In the above description, certain terms have been used for brevity, clarity, and understanding. No unnecessary limitations are to be inferred therefrom beyond the requirement of the prior art because such terms are used for descriptive purposes and are intended to be broadly construed. The different assemblies described herein may be used alone or in combination with other devices. It is to be expected that various equivalents, alternatives and modifications are possible within the scope of any appended claims.

We claim:

1. A device configured to provide phototherapy to a patient, the device being configured to be supported by a base on the ground, the device comprising:
   a plurality of lights configured to emit irradiance to provide phototherapy, wherein the plurality of lights is positionable to emit the irradiance towards the patient;
   an enclosure that is connected to the base and supports the plurality of lights;
   a control module that is operatively connected to the plurality of lights, wherein the control module controls the irradiance emitted from the plurality of lights;
   a non-transitory memory module that is operatively connected to the control module;
   a plurality of sensors that are operatively connected to the control module, wherein the plurality of sensors is configured to sense a current position of the plurality of lights, wherein the current position sensed by the plurality of sensors comprises an angle between the plurality of lights and the base; and a control program configured to receive inputs and to provide outputs, wherein the non-transitory memory module stores the control program, wherein the inputs include at least the current position of the plurality of lights, wherein the control program determines the outputs based at least in part on the inputs, and wherein the outputs are provided by the control program to the control module;

wherein the control module controls the irradiance emitted from the plurality of lights based at least in part on the outputs provided by the control program.

2. The device according to claim 1, wherein the current position sensed by the plurality of sensors includes a height between the plurality of lights and the ground.

3. The device according to claim 2, wherein the height is sensed by a piezo-electric sensor.

4. The device according to claim 1, wherein the current position sensed by the plurality of sensors includes a distance between the plurality of lights and a target.

5. The device according to claim 4, wherein the target is the patient and wherein the distance is sensed by an optical sensor.

6. The device according to claim 1, further comprising an irradiance sensor, wherein the irradiance sensor senses an actual irradiance being emitted by the plurality of lights, and wherein the control module also controls the irradiance emitted from the plurality of lights based at least in part on the actual irradiance.

7. The device according to claim 1, wherein a current flows through the plurality of lights, and wherein a current sensor is configured to sense the current flowing through the plurality of lights.

8. The device according to claim 7, further comprising an indicator, wherein the control module is configured to monitor the current flowing through the plurality of lights over time, wherein the control program further includes a replacement threshold for the current flowing through the plurality of lights, and wherein the indicator provides an indication when at least one light of the plurality of lights violates the replacement threshold.

9. The device according to claim 1, wherein the plurality of lights is an array of light emitting diodes, and wherein each light of the plurality of lights is controlled by the control module independently.

10. The device according to claim 1, wherein the control module controls the irradiance emitted from the plurality of lights by controlling a plurality of currents provided thereto.

11. The device according to claim 1, wherein the control program further includes safety protocols, wherein the control module controls the irradiance emitted from the plurality of lights such that the safety protocols are not violated.

12. A method for providing phototherapy to a patient, the method comprising:

positioning a plurality of lights to emit irradiance towards the patient;

operatively connecting a control module to the plurality of lights, wherein the control module controls the irradiance emitted from the plurality of lights;

operatively connecting a non-transitory memory module to the control module;

operatively connecting a plurality of sensors to the control module;

sensing with the plurality of sensors a current position of the plurality of lights, wherein the current position sensed by the plurality of sensors comprises an angle between the plurality of lights and a base;

storing a control program within the non-transitory memory and configuring the control program to receive inputs and to provide outputs, wherein the inputs include at least the current position of the plurality of lights;

determining with the control program the outputs based at least in part on the inputs received by the control program and providing the outputs to the control module; and controlling with the control module the irradiance emitted from the plurality of lights based at least in part on the outputs provided by the control program.

13. The method according to claim 12, wherein the plurality of lights are supported by a base on the ground, wherein sensing the current position sensed by the plurality of sensors further comprises sensing a height between the plurality of lights and the ground, and sensing a distance between the plurality of lights and a target, further comprising sensing a current flowing through the plurality of lights, and further comprising sensing an actual irradiance being emitted by the plurality of lights, wherein the inputs received by the control program include at least the angle, the height, the distance, the current, and the irradiance.

14. The method according to claim 12, wherein each light of the plurality of lights is controlled by the control module independently.

15. The method of claim 13, further comprising sensing the height with a piezo-electric sensor.

16. The method of claim 13, wherein the target is the patient, and wherein the distance is sensed by an optical sensor.

17. The method of claim 13, further comprising:

monitoring the current flowing through the plurality of lights over time;

detecting a replacement threshold for the current flowing through the plurality of lights; and providing an indicator when at least one light of the plurality of lights violates the replacement threshold.

18. The method of claim 13, wherein the plurality of lights comprises an array of light emitting diodes.

19. The method of claim 13, further comprising detecting safety protocols and controlling the irradiance emitted from the plurality of lights such that the safety protocols are not violated.

* * * * *